(12) United States Patent
Soya et al.

(10) Patent No.: US 9,493,433 B2
(45) Date of Patent: Nov. 15, 2016

(54) METHOD FOR PRESERVING AQUEOUS SOLUTION CONTAINING LEUCO CHROMOGEN

(75) Inventors: Haruyo Soya, Sunto-gun (JP); Tomomi Murakami, Sunto-gun (JP); Haruki Tsunoda, Sunto-gun (JP); Yu Ohsugi, Sunto-gun (JP); Ayako Yoda, Sunto-gun (JP); Masashi Matsushita, Sunto-gun (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 13/811,925

(22) PCT Filed: Aug. 9, 2011

(86) PCT No.: PCT/JP2011/068105
§ 371 (c)(1),
(2), (4) Date: Jan. 24, 2013

(87) PCT Pub. No.: WO2012/020746
PCT Pub. Date: Feb. 16, 2012

(65) Prior Publication Data
US 2013/0123491 A1    May 16, 2013

(30) Foreign Application Priority Data

Aug. 11, 2010 (JP) ................................ 2010-180564

(51) Int. Cl.
| | | |
|---|---|---|
| *C09B 21/00* | (2006.01) | |
| *C09B 67/00* | (2006.01) | |
| *C09B 67/42* | (2006.01) | |
| *C07D 279/30* | (2006.01) | |
| *C09B 67/28* | (2006.01) | |
| *C09B 67/44* | (2006.01) | |
| *C12Q 1/28* | (2006.01) | |
| *G01N 33/72* | (2006.01) | |
| *C09B 11/12* | (2006.01) | |

(52) U.S. Cl.
CPC ............. *C07D 279/30* (2013.01); *C09B 11/12* (2013.01); *C09B 21/00* (2013.01); *C09B 67/0077* (2013.01); *C09B 67/0083* (2013.01); *C12Q 1/28* (2013.01); *G01N 33/723* (2013.01)

(58) Field of Classification Search
CPC .... D06P 1/30; D06P 1/5278; D06P 1/65131; D06P 1/60; D06P 1/613; C09B 9/00; C09B 9/02; C09B 21/00; C09B 67/0077; C09B 67/0083; C09B 67/42; C09B 67/0089; C09B 67/009; C07D 279/30; C12Q 1/28; G01N 33/723
USPC ..................................... 8/552, 657, 651, 652
See application file for complete search history.

(56) References Cited

U.S. PATENT DOCUMENTS

2006/0014229 A1* 1/2006 Katayama et al. ............. 435/11

FOREIGN PATENT DOCUMENTS

| | | |
|---|---|---|
| GB | 1 433 469 | 4/1976 |
| JP | 57-029297 | 2/1982 |
| JP | 62-093261 | 4/1987 |
| JP | 03-206896 | 9/1991 |
| JP | 07-051095 | 2/1995 |
| JP | 2005-110507 | 4/2005 |
| JP | 2006-022215 | 1/2006 |
| JP | 2008-201968 | 9/2008 |
| JP | 2013-141453 | 7/2013 |
| WO | 2005/088305 | 9/2005 |
| WO | 2007-083703 | 7/2007 |
| WO | 2009/069309 | 6/2009 |
| WO | 2009/069310 | 6/2009 |

OTHER PUBLICATIONS

Aoyama, "H2O2-POD System", Journal of Medical Technology, vol. 41, No. 9 (1997) 1014-19.

* cited by examiner

*Primary Examiner* — Amina Khan
(74) *Attorney, Agent, or Firm* — Fitzpatrick, Cella, Harper & Scinto

(57) ABSTRACT

Described is a method for preserving an aqueous solution comprising a leuco chromogen, comprising adding at least one compound selected from the group consisting of polyoxyethylene alkylamine and polyoxyethylene alkenylamine to the aqueous solution containing a leuco chromogen, and a method for stabilizing a leuco chromogen, comprising allowing the leuco chromogen to coexist in an aqueous solution comprising at least one compound selected from the group consisting of polyoxyethylene alkylamine and polyoxyethylene alkenylamine.

6 Claims, No Drawings

METHOD FOR PRESERVING AQUEOUS SOLUTION CONTAINING LEUCO CHROMOGEN

This application is a National Phase of PCT Application No. PCT/JP2011/068105 filed Aug. 9, 2011, which in turn claims benefit of Japanese Patent Application No. 2010-180564 filed Aug. 11, 2010.

TECHNICAL FIELD

The present invention relates to a method for preserving an aqueous solution containing a leuco chromogen, a method for stabilizing a leuco chromogen, and a liquid reagent containing a leuco chromogen.

BACKGROUND ART

A leuco chromogen is a chromogen that generates a dye through reaction with hydrogen peroxide in the presence of a peroxidatively active substance such as peroxidase. This type of chromogen, unlike coupling-type chromogens, generates a dye in itself and known leuco chromogens include, for example, phenothiazine leuco chromogens, triphenylmethane leuco chromogens, and diphenylamine leuco chromogens (see e.g., Patent Documents 1 to 3).

The leuco chromogen is often used, as in coupling-type chromogens, in the quantification of an analyte component such as cholesterol or glycated hemoglobin contained in a sample such as serum. Specifically, clinical laboratory examinations often involve: converting an analyte component in a sample to hydrogen peroxide; reacting the generated hydrogen peroxide with a leuco chromogen in the presence of a peroxidatively active substance such as peroxidase to convert the chromogen to a dye; and quantifying the analyte component in the sample on the basis of the absorbance of the generated dye. Particularly, the leuco chromogen is preferably used as a highly sensitive chromogen in the quantification of an analyte component contained only in a trace amount in a sample (see e.g., Non-patent Document 1).

The leuco chromogen is used as a highly sensitive chromogen, as described above, in the quantification of a trace amount of an analyte component in a sample, whereas the leuco chromogen has poor storage stability and undesirably develops color spontaneously with time, particularly, in a solution. To cope with this undesirable poor stability of the leuco chromogen, methods for stabilizing the leuco chromogen in a solution have been studied and reported so far (see e.g., Patent Documents 4 and 5). Unfortunately, these methods for stabilizing the leuco chromogen are not always satisfactory, for example, because they must be performed under strict conditions.

PRIOR ART DOCUMENTS

Patent Documents

Patent Document 1: Japanese unexamined Patent Application Publication No. 57-029297
Patent Document 2: Japanese unexamined Patent Application Publication No. 3-206896
Patent Document 3: Japanese unexamined Patent Application Publication No. 62-093261
Patent Document 4: WO2005/088305
Patent Document 5: WO2007/083703

Non-Patent Documents

Non-patent Document 1: Journal of Medical Technology, 1997, Vol. 41, No. 9, p. 1014-1019

SUMMARY OF THE INVENTION

Problems to be Solved by the Invention

An object of the present invention is to provide a method for preserving an aqueous solution containing a leuco chromogen, a method for stabilizing a leuco chromogen, whereby the leuco chromogen is stably preserved in an aqueous solution, and a reagent for stably retaining a leuco chromogen.

Means to Solve the Problems

The present inventors have conducted diligent studies to solve the problems and consequently found that at least one compound selected from the group consisting of polyoxyethylene alkylamine and polyoxyethylene alkenylamine is added to an aqueous solution containing a leuco chromogen, whereby the leuco chromogen is stably preserved. On the basis of these findings, the present invention has been completed. Specifically, the present invention relates to the following [1] to [7]:

[1] A method for preserving an aqueous solution containing a leuco chromogen, comprising adding at least one compound selected from the group consisting of polyoxyethylene alkylamine and polyoxyethylene alkenylamine to the aqueous solution containing a leuco chromogen.
[2] A method for stabilizing a leuco chromogen, comprising allowing the leuco chromogen to coexist in an aqueous solution comprising at least one compound selected from the group consisting of polyoxyethylene alkylamine and polyoxyethylene alkenylamine.
[3] The method according to [1] or [2], wherein the leuco chromogen is a phenothiazine chromogen.
[4] The method according to [3], wherein the phenothiazine chromogen is 10-(carboxymethylaminocarbonyl)-3,7-bis(dimethylamino)phenothiazine.
[5] A liquid reagent comprising a leuco chromogen and at least one compound selected from the group consisting of polyoxyethylene alkylamine and polyoxyethylene alkenylamine.
[6] The reagent according to [5], wherein the leuco chromogen is a phenothiazine chromogen.
[7] The reagent according to [6], wherein the phenothiazine chromogen is 10-(carboxymethylaminocarbonyl)-3,7-bis(dimethylamino)phenothiazine.

Effect of the Invention

The present invention provides a method for preserving an aqueous solution containing a leuco chromogen and a method for stabilizing a leuco chromogen, whereby the leuco chromogen is stably preserved in an aqueous solution, and a liquid reagent containing a leuco chromogen. The method and the reagent of the present invention are useful in, for example, measurement of glycated hemoglobin used in the diagnosis of diabetes mellitus.

MODE FOR CARRYING OUT THE INVENTION (1) Method for Preserving Aqueous Solution Containing Leuco Chromogen and Method for Stabilizing Leuco Chromogen The present invention relates to a method for preserving an aqueous solution containing a leuco chromogen. According to the method for preserving an aqueous solution containing a leuco chromogen according to the present invention, a leuco chromogen is stably preserved in an aqueous solution. In the present invention, the phrase "leuco chromogen is stably preserved in an aqueous solution" means that the leuco chromogen in the aqueous solution is stable against heat or stable against light, preferably, stable against heat and light. In the method for preserving an aqueous solution containing a leuco chromogen according to the present invention, at least one compound selected from the group consisting of polyoxyethylene alkylamine and polyoxyethylene alkenylamine is added to the aqueous solution containing a leuco chromogen. Examples of alkyl in the polyoxyethylene alkylamine (hereinafter, referred to as POE alkylamine) according to the present invention include alkyl having 8 to 20 carbon atoms. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. The degree of polymerization of oxyethylene in the POE alkylamine is, for example, 1 to 24.

Specific examples (products) of the POE alkylamine include Nymeen L-201(oxyethylene dodecylamine; manufactured by NOF Corp.), Nymeen L-202, Nymeen L-207, and Nymeen L-215 (all polyoxyethylene dodecylamine; manufactured by NOF Corp.), Nymeen S-202, Nymeen S-204, Nymeen S-210, Nymeen S-215, and Nymeen S-220 (all polyoxyethylene octadecylamine; manufactured by NOF Corp.), Nymeen T2-202, Nymeen T2-210, and Nymeen T2-230 [all polyoxyethylene alkyl (beef tallow) amine; manufactured by NOF Corp.], Nymeen F-202, Nymeen F-203, Nymeen F-205, Nymeen F-210, and Nymeen F-215 [all polyoxyethylene alkyl (coconut oil) amine; manufactured by NOF Corp.], Blaunon L-202, Blaunon L-205, Blaunon L-207, Blaunon L-210, and Blaunon L-230 (all polyoxyethylene dodecylamine; manufactured by Aoki Oil Industrial Co., Ltd.), Blaunon S-207, Blaunon S-210, Blaunon S-215, Blaunon S-220, and Blaunon S-230 (all polyoxyethylene octadecylamine; manufactured by Aoki Oil Industrial Co., Ltd.), Blaunon S-205T, Blaunon S-208T, Blaunon S-210T, Blaunon S-215T, and Blaunon S-230T [all polyoxyethylene alkyl (beef tallow) amine; manufactured by Aoki Oil Industrial Co., Ltd.], Newcol OD420 (polyoxyethylene octadecylamine; manufactured by Nippon Nyukazai Co. Ltd.), Pionin D3104 (polyoxyethylene dodecylamine; manufactured by Takemoto Oil & Fat Co., Ltd.), Pionin D3110 (polyoxyethylene dodecylamine; manufactured by Takemoto Oil & Fat Co., Ltd.), Pionin D3605 [polyoxyethylene alkyl (soybean) amine; manufactured by Takemoto Oil & Fat Co., Ltd.], and Pionin D3615T [polyoxyethylene alkyl (beef tallow) amine; manufactured by Takemoto Oil & Fat Co., Ltd.].

Examples of alkenyl in the polyoxyethylene alkenylamine (hereinafter, referred to as POE alkenylamine) according to the present invention include alkenyl having 8 to 20 carbon atoms. Examples of the alkenyl having 8 to 20 carbon atoms include octenyl, nonenyl, decenyl, citronellyl, undecenyl, dodecenyl, tridecenyl, tetradecenyl, pentadecenyl, hexadecenyl, heptadecenyl, oleyl, nonadecenyl, and eicosenyl. The degree of polymerization of oxyethylene in the POE alkenylamine is, for example, 1 to 24.

Specific examples (products) of the POE alkenylamine include BLAUNON 0209 (polyoxyethylene oleylamine; manufactured by Aoki Oil Industrial Co., Ltd.).

In the method for preserving an aqueous solution containing a leuco chromogen according to the present invention, a concentration of the POE alkylamine or the POE alkenylamine is usually 0.0001 to 10%, preferably 0.0005 to 5%.

In the method for preserving a leuco chromogen according to the present invention, the storage stability of the leuco chromogen can be evaluated on the basis of the coloring of the aqueous solution containing the leuco chromogen. It can be evaluated that stronger the coloring, i.e., larger the absorbance of the aqueous solution containing a leuco chromogen, the stability of leuco chromogen in the solution is worse. By contrast, it can be evaluated that weaker the coloring, i.e., smaller the absorbance of the aqueous solution containing a leuco chromogen, the stability of leuco chromogen in the solution is better.

The aqueous solution containing a leuco chromogen according to the present invention refers to an aqueous solution containing a leuco chromogen dissolved in an aqueous medium and can be prepared by adding and dissolving the leuco chromogen in the aqueous medium. The aqueous medium in which the leuco chromogen is dissolved is not particularly limited as long as the aqueous medium is capable of dissolving therein the leuco chromogen. Examples thereof include deionized water, distilled water, and buffer solution. A buffer solution is preferable. For the preparation of the aqueous solution containing a leuco chromogen, an organic solvent can be used as a solubilizer that makes the leuco chromogen soluble in the aqueous medium. The leuco chromogen dissolved in the organic solvent can be added to the aqueous medium and dissolved in this aqueous medium to prepare the aqueous solution containing the leuco chromogen. The organic solvent is not particularly limited as long as the organic solvent is capable of dissolving therein the leuco chromogen. Examples thereof include dimethylformamide (DMF), dimethyl sulfoxide (DMSO), dioxane, acetone, methanol, and ethanol.

The pH of the aqueous medium is not particularly limited as long as the leuco chromogen is dissolved. The pH is, for example, 4 to 10. In the case of using a buffer solution as the aqueous medium, a buffer is preferably used according to the set pH. Examples of the buffer used in the buffer solution include a tris(hydroxymethyl)aminomethane buffer, a phosphate buffer, a borate buffer, and Good's buffers.

Examples of the Good's buffers include 2-morpholinoethanesulfonic acid (MES), bis (2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of the buffer solution is not particularly limited as long as the leuco chromogen is dissolved. The concentration is usually 0.001 to 2.0 mol/L, preferably 0.005 to 1.0 mol/L.

Examples of the leuco chromogen according to the present invention include phenothiazine chromogens, triphenylmethane chromogens, diphenylamine chromogens, o-phenylenediamine, hydroxypropionic acid, diaminobenzidine, and tetramethylbenzidine. A phenothiazine chromogen is preferable. Examples of the phenothiazine chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among these phenothiazine chromogens, 10-N-(carboxymethylaminocarbonyl)-3,7-bis(dimethylamino)-10H-phenothiazine sodium salt (DA-67) is particularly preferable. Examples of the triphenylmethane chromogens include N,N,N',N',N'',N''-hexa(3-sulfopropyl)-4,4',4''-triaminotriphenylmethane (TPM-PS). Examples of the diphenylamine chromogens include N-(carboxymethylaminocarbonyl)-4,4'-bis(dimethylamino)diphenylamine sodium salt (DA-64), 4,4'-bis(dimethylamino)diphenylamine, and bis[3-bis(4-chlorophenyl)methyl-4-dimethylaminophenyl]amine (BCMA).

The present invention further relates to a method for stabilizing a leuco chromogen. The stabilization of a leuco chromogen according to the present invention means that the leuco chromogen in an aqueous solution containing the leuco chromogen is stabilized against heat or stabilized against light, preferably, stabilized against heat and light. In this context, the stabilization of the leuco chromogen can be evaluated on the basis of the coloring of the aqueous solution containing this leuco chromogen. It can be evaluated that stronger the coloring, i.e., larger the absorbance of the aqueous solution containing a leuco chromogen, the stability of leuco chromogen in the solution is worse. By contrast, it can be evaluated that weaker the coloring, i.e., smaller the absorbance of the aqueous solution containing a leuco chromogen, the stability of leuco chromogen in the solution is better.

In the method for stabilizing a leuco chromogen according to the present invention, the leuco chromogen is allowed to coexist in an aqueous solution comprising at least one compound selected from the group consisting of POE alkylamine and POE alkenylamine. Examples of the POE alkylamine and the POE alkenylamine used in the method for stabilizing a leuco chromogen according to the present invention include the aforementioned POE alkylamine and the POE alkenylamine.

Examples of the leuco chromogen and the aqueous solution containing a leuco chromogen used in the stabilization method of the present invention include the aforementioned leuco chromogen and the aforementioned aqueous solution containing a leuco chromogen, respectively, in the method for preserving a leuco chromogen. In the present invention, a concentration of the leuco chromogen in the aqueous solution containing the leuco chromogen is not particularly limited as long as the leuco chromogen is dissolved in the aqueous medium, and is usually 0.0001 to 2.0 mmol/L, preferably 0.0005 to 1.0 mmol/L.

In the present invention, a concentration of the POE alkylamine or the POE alkenylamine coexisting with the leuco chromogen in the aqueous solution is usually 0.0001 to 10%, preferably 0.0005 to 5%.

In the present invention, the method for determining the stability of the leuco chromogen against heat is not particularly limited as long as the method is capable of determining the stability of the leuco chromogen against heat. Examples thereof include a method involving storing the aqueous solution containing the leuco chromogen at 5° C. or 30° C. and then determining the coloring of the aqueous solution using an absorption spectrometer.

Also, in the present invention, the method for determining the stability of the leuco chromogen against light is not particularly limited as long as the method is capable of determining the stability of the leuco chromogen against light. Examples thereof include a method involving irradiating the aqueous solution containing the leuco chromogen with light for 15 hours and then determining the coloring of the aqueous solution thus irradiated using an absorption spectrometer.

(2) Liquid Reagent

The liquid reagent of the present invention comprises a leuco chromogen and at least one compound selected from the group consisting of POE alkylamine and POE alkenylamine.

In the liquid reagent of the present invention, the leuco chromogen coexists with at least one compound selected from the group consisting of POE alkylamine and POE alkenylamine in an aqueous medium. Examples of the leuco chromogen in the liquid reagent of the present invention include the aforementioned leuco chromogen. Examples of the aqueous medium in the liquid reagent of the present invention include the aforementioned aqueous medium. Examples of the POE alkylamine and the POE alkenylamine in the liquid reagent of the present invention include the aforementioned POE alkylamine and the POE alkenylamine, respectively.

A concentration of the POE alkylamine or the POE alkenylamine in the liquid reagent of the present invention is usually 0.0001 to 10%, preferably 0.0005 to 5%. A concentration of the leuco chromogen in the liquid reagent of the present invention is not particularly limited as long as the leuco chromogen is dissolved in the aqueous medium, and is usually 0.0001 to 2.0 mmol/L, preferably 0.0005 to 1.0 mmol/L. The aforementioned organic solvent can be used as a solubilizer for the dissolution of the leuco chromogen in the aqueous medium.

Hereinafter, the present invention will be described in more detail with reference to Examples. However, the scope of the present invention is not limited to these examples by any means.

In Examples, Comparative Examples, and Test Examples below, reagents and enzymes from the following manufacturers were used.

Bis-Tris (manufactured by Dojindo Laboratories), peroxidase (manufactured by Toyobo Co., Ltd.), 30% aqueous hydrogen peroxide solution (manufactured by Wako Pure Chemical Industries, Ltd.), bovine serum albumin (BSA; manufactured by Proliant Inc.), Nymeen S210 [polyoxyethylene (10) stearylamine; manufactured by NOF Corp.], and Nymeen S220 [polyoxyethylene (20) stearylamine; manufactured by NOF Corp.].

EXAMPLE 1

(1) Preparation of Aqueous Solution Containing DA-67 and Sample for DA-67 Stability Assay An aqueous solution containing DA-67 was prepared according to the following composition:

<Aqueous Solution Containing DA-67>

| Bis-Tris (pH 7.0) | 10 mmol/L |
|---|---|
| DA-67 | 20 µmol/L |
| Surfactant (see Table 1) | 0.5% |

Each DA-67-containing aqueous solution having this composition was stored at 5° C. for 7 days or at 30° C. for 7 days. The resulting solutions were used as samples for DA-67 stability assay.

(2) Preparation of Reagent for DA-67 Stability Assay

A reagent for DA-67 stability assay was prepared according to the following composition:

<Reagent for DA-67 Stability Assay>

| Bis-Tris (pH 7.0) | 10 mmol/L |
|---|---|
| BSA | 0.005% |

(3) Evaluation of Stability of DA-67 in DA-67-Containing Aqueous Solution

120 µl of the reagent for DA-67 stability assay prepared in the paragraph (2) was added to 30 µl of the freshly-prepared DA-67-containing aqueous solution, and the mixture was heated at 37° C. for 5 minutes. Then, the absorbance ($E_{freshly\text{-}prepared}$) of the solution was measured at a primary wavelength of 660 nm and a secondary wavelength of 800 nm using Hitachi 7170S automatic analyzer. The same assay was conducted using the reagent for DA-67 stability assay of (2) instead of the freshly-prepared DA-67-containing aqueous solution to determine the absorbance ($E_{blank}$). $E_{blank}$ was subtracted from $E_{freshly\text{-}prepared}$ to determine the absorbance ($\Delta E_{freshly\text{-}prepared}$) for the freshly-prepared DA-67-containing aqueous solution.

Similarly, the DA-67-containing aqueous solution stored at 5° C. for 7 days and the DA-67-containing aqueous solution stored at 30° C. for 7 days were assayed as samples to determine the absorbance ($\Delta E_{5°\,C.}$) for the DA-67-containing aqueous solution stored at 5° C. for 7 days and the absorbance ($\Delta E_{30°\,C.}$) for the DA-67-containing aqueous solution stored at 30° C. for 7 days.

$\Delta E_{freshly\text{-}prepared}$ was subtracted from each of $\Delta E_{5°\,C.}$ and $\Delta E_{30°\,C.}$ thus determined. The determined values were designated as $\Delta E_1$ and $\Delta E_2$, respectively, and used as indexes for the stability of DA-67. The results are shown in Table 1. Both the values of $\Delta E_1$ and $\Delta E_2$ closer to 0 represent that the aqueous solution is prevented from being colored and DA-67 is stably preserved in the aqueous solution, i.e., DA-67 is stabilized in the aqueous solution.

TABLE 1

| | Change in absorbance after 7-day storage | |
|---|---|---|
| Surfactant | $\Delta E_1$ (Stored at 5° C.) | $\Delta E_2$ (Stored at 30° C.) |
| — | 0.002 | 0.023 |
| Nymeen S210 | 0.000 | 0.002 |
| Nymeen S220 | 0.002 | 0.002 |

As shown in Table 1, the aqueous solution comprising POE alkylamine was significantly prevented from being colored after storage both at 5° C. and at 30° C., compared with the aqueous solution free from POE alkylamine. It proved that DA-67 in the aqueous solution comprising POE alkylamine was stable against heat and the DA-67-containing aqueous solution was stably preserved by POE alkylamine, i.e., DA-67 was stabilized in the aqueous solution by POE alkylamine.

EXAMPLE 2

The DA-67-containing aqueous solution prepared in Example 1 was irradiated with 1100 lux of light for 15 hours to evaluate the light stability of DA-67. The DA-67-containing aqueous solution after light irradiation was used as a sample in the same way as in Example 1 to determine the absorbance $\Delta E_3$ for the DA-67-containing aqueous solution after light irradiation. The assay results are shown in Table 2.

TABLE 2

| Surfactant | $\Delta E_3$ (Change in absorbance after 15-hr light irradiation) |
|---|---|
| — | 0.064 |
| Nymeen S210 | 0.000 |
| Nymeen S220 | 0.000 |

As shown in Table 2, the aqueous solution comprising POE alkylamine was significantly prevented from being colored due to light irradiation, compared with the aqueous solution free from POE alkylamine. It proved that DA-67 in the aqueous solution comprising POE alkylamine was stable against light and the DA-67-containing aqueous solution was stably preserved by POE alkylamine, i.e., DA-67 was stabilized by POE alkylamine.

INDUSTRIAL APPLICABILITY

The present invention provides a method for preserving an aqueous solution containing a leuco chromogen, a method for stabilizing a leuco chromogen, and a liquid reagent comprising a leuco chromogen. The method and the reagent of the present invention are useful in, for example, measurement of glycated hemoglobin used in the diagnosis of diabetes mellitus.

The invention claimed is:

1. A method for stabilizing a leuco chromogen, comprising allowing the leuco chromogen to coexist for at least seven days in an aqueous solution comprising at least one compound selected from the group consisting of polyoxyethylene alkylamine with an alkyl having 8 to 20 carbon atoms and polyoxyethylene alkenylamine with an alkenyl having 8 to 20 carbon atoms, wherein
   the leuco chromogen is a phenothiazine chromogen selected from the group consisting of 10-N-(carboxymethylaminocarbonyl)-3,7-bis(dimethylamino)-10H-phenothiazine contained at a concentration of 0.0001 to 2.0 mmol/L and 10-N-methylcarbamoyl-3,7-bis(dimethylamino)-10H-phenothiazine contained at a concentration of 0.1 to 2.0 mmol/L in said aqueous solution, and
   the polyoxyethylene alkylamine or the polyoxyethylene alkenylamine is contained at a concentration of 0.5 to 5% in said aqueous solution.

2. The method according to claim 1, wherein the phenothiazine chromogen is 10-N-(carboxymethylaminocarbonyl)-3,7-bis(dimethylamino)-10H-phenothiazine.

3. The method according to claim 1, wherein the leuco chromogen is 10-N-(carboxymethylaminocarbonyl)-3,7-bis(dimethylamino)-10H-phenothiazine contained at a concentration of 0.0005 to 1.0 mmol/L in said aqueous solution.

4. The method according to claim 1, wherein the degree of polymerization of oxyethylene in the polyoxyethylene alkylamine is 1-24, and the degree of polymerization of oxyethylene in the polyoxyethylene alkenylamine is 1-24.

5. The method according to claim 2, wherein the degree of polymerization of oxyethylene in the polyoxyethylene alkylamine is 1-24, and the degree of polymerization of oxyethylene in the polyoxyethylene alkenylamine is 1-24.

6. The method according to claim 3, wherein the degree of polymerization of oxyethylene in the polyoxyethylene alkylamine is 1-24, and the degree of polymerization of oxyethylene in the polyoxyethylene alkenylamine is 1-24.

* * * * *